United States Patent [19]

Raghu

[11] 4,245,103

[45] Jan. 13, 1981

[54] PROCESSES FOR THE PREPARATION OF TETRAMISOLE

[75] Inventor: Sivaraman Raghu, Norwalk, Conn.

[73] Assignee: American Cyanamid Company, Stamford, Conn.

[21] Appl. No.: 63,289

[22] Filed: Aug. 2, 1979

Related U.S. Application Data

[63] Continuation of Ser. No. 958,222, Nov. 6, 1978, abandoned.

[51] Int. Cl.³ ............................................. C07D 277/60
[52] U.S. Cl. ................................................... 548/155
[58] Field of Search ........................................ 548/155

[56] References Cited

U.S. PATENT DOCUMENTS

| | | | |
|---|---|---|---|
| 3,855,234 | 12/1974 | Roy ........................................ | 548/155 |
| 3,873,560 | 3/1975 | McMenim ............................. | 548/155 |
| 3,890,341 | 6/1975 | Gordon et al. ....................... | 548/155 |

*Primary Examiner*—N. S. Rizzo
*Attorney, Agent, or Firm*—Harry H. Kline

[57] ABSTRACT

Processes for reacting arylvinyl oxides and alkoxyethylamines to provide novel N-substituted alkoxyethylamines; processes for reacting the novel N-substituted amines with nitriles to provide novel amidoamines; processes for preparing novel diamines from the amidoamines, together with the novel nitrogen-containing products so produced, such products being useful for the preparation of various imidazothiazoles including tetramisole.

5 Claims, No Drawings

PROCESSES FOR THE PREPARATION OF TETRAMISOLE

This application is a continuation of our copending application, Ser. No. 958,222, filed Nov. 6, 1978 now abandoned.

BACKGROUND OF THE INVENTION

The present invention relates to processes for the preparation of novel aryl substituted nitrogen compounds, and more particularly, it relates to improved processes useful for the production of pharmaceutically desirable aryl imidazothiazoles, as well as to novel intermediate compounds obtained through such processes.

Certain imidazothiazoles have been found to have useful pharmaceutical and veterinary activity. For instance, the synthesis of tetramisole, or racemic 2,3,5,6-tetrahydro-6-phenylimidazo[2,1-b]thiazole, and its pharmaceutically acceptable addition salts is of considerable commercial interest because of the anthelminthic activity of such compounds. The enantiomers of this compound are well known and the laevorotatory isomer is extremely well suited to such uses, as discussed in U.S. Pat. No. 3,463,786.

As a consequence of such activity, various syntheses are known. In this connection, there are cited Raeymaekers et al, *J. Med. Chem.* 9, 545 (1966); Bakelien et al, *Aust J. Chem.* 21, 1557 (1968); Roy U.S. Pat. No. 3,855,234; McMemin U.S. Pat. No. 3,845,070; and Spicer U.S. Pat. No. 3,726,894.

The method used by Raeymaekers prescribes a reduction step involving sodium borohydride, a relatively expensive reducing agent, while Bakelien utilizes aziridine, the carcinogenicity of which renders it most undesirable for use in the manufacture of pharmaceutically active material. The procedures described in U.S. Pat. Nos. 3,845,070 and 3,726,894 lack regioselectivity in the first step of the reaction. This step involves reacting styrene oxide with either aziridine or 2-ethanolamine and results in a mixture of two isomers because the amine is attached at the primary, or benzylic, carbon atom of the styrene oxide.

U.S. Pat. Nos. 3,873,560 and 3,925,440 show two processes for producing tetramisole from N-(2-hydroxy-2-phenethyl) ethanolamine. These processes proceed, respectively, by way of 3-(2-amino-2-phenethyl)thiazolidin2-thione and 3-(2-amino-2-phenethyl)-2-iminothiazolidine as intermediates. In each of these processes, the starting compound is not produced regioselectively, as is also true of aforementioned U.S. Pat. Nos. 3,845,070 and 3,726,894. It will be appreciated that the failure to use regioselective processes results in lower yields and can also cause difficulties in the separation and isolation of desired products.

U.S. Pat. No. 3,726,894 synthesizes tetramisole by reaction of 1-(2-hydroxyethyl)-4-phenylimidazolidin-2-thione with thionyl chloride, followed by treatment with a base. One disadvantage of this synthesis scheme is that the thione is prepared by hydroboration of 1-vinyl-4-phenylimidazolidin-2-thione, a commercially difficult step, and the vinyl starting compound is itself a degradation side product of tetramisole. This side product arises during racemization of the physiologically inactive d-enantiomer of tetramisole to the physiologically active d,l-tetramisole. Accordingly, the procedure is not a practical, independent synthesis of the starting compound.

The available literature reports other methods for synthesizing tetramisole, but all of them lack regioselectivity and have the capability of producing a mixture of tetramisole and so-called isotetramisole. Thus, the method described by Raeymaekers et al, *Tetrahedron Letters*, 1467 (1967) contemplates the reaction of 4-phenylimidazolidin-2-thione with ethylene bromide.

French Pat. No. 2,264,017 describes the synthesis of tetramisole through the reaction of a 2-bromo-4-phenylimidazoline with 2-chloroethanethiol, followed by cyclization. French Pat. Nos. 2,258,379 and 2,258,380 describe the synthesis of tetramisole by serially reacting 4-phenylimidazolidin-2-thione with chloroethanol and ethylene oxide and further cyclizing to obtain tetramisole. It is evident from these references that the cyclization is effected with equal facility on either of the two imidazolidine ring nitrogen atoms, so these processes inevitably produce a mixture of tetramisole and isotetramisole. French Pat. No. 2,264,018 sets forth a synthesis of tetramisole by reacting 1-(2-bromoethyl)-4-phenyl-2-choloroimidazoline with sodium sulfide, but there is no disclosure as to how the former compound isto be synthesized.

THE INVENTION

The present invention provides novel and economical processes for the preparation of intermediates for ultimate preparation of arylimidazothiazoles. The intermediates are prepared from relatively available starting materials, and the processes themselves provide good yields. These factors, together with ease of handling, ease of recovery, and flexibility of operation provide for an uncomplicated and economical procedure. In addition, the processes of the present invention readily provide novel amines and amine derivatives.

Briefly, the processes of the present invention comprise reacting an arylvinyl oxide with an alkoxyethylamine to produce N-substituted alkoxyethylamines in good yields. The N-substituted alkoxyethylamines can thereafter be reacted with a nitrile to provide an amidoamine which is readily hydrolyzed to obtain a novel diamine. The diamine so produced can be treated by sulfurization to form an imidazole which is thereafter reacted with specific acids to provide an imidazothiazole salt. The imidazothiazole itself can thereafter be obtained by simple hydrolysis with a base. The novel intermediate compounds provided by the steps and processes of the present invention are disclosed in more detail herein.

The arylvinyl oxide starting material used in the practice of the present invention has the general formula

(I).

Ar represents a substituted or unsubstituted mono- or polynuclear aromatic substituent. Thus, the aryl group can include phenyl, tolyl, xylyl, naphthyl, phenanthryl, and like groups. It is also contemplated in certain desirable embodiments of the present invention that the aryl groups can be mono- or polyhalo or mono- or polynitro-substituted, such as chlorophenyl, nitrophenyl, and the like. In certain embodiments, phenyl is a preferred aryl group.

The arylvinyl oxide is reacted with an alkoxyethylamine having the formula $H_2N-CH_2-CH_2-OR_1$ (II), where $R_1$ is a hydrocarbon group. It is desirable for reasons of availability, yield, and economy that $R_1$ represent alkyl groups. Preferred alkyl groups used in the practice of this process are the lower alkyl groups, particularly those containing from one to six carbon atoms. Examples of such groups are methyl, ethyl, propyl, butyl, isopropyl, isobutyl, amyl, and hexyl. In certain embodiments, methoxyethylamine is especially preferred.

The reaction of the arylvinyl oxide and the alkoxyethylamine provides novel N-substituted alkoxyethylamines in high yields and with surprising regioselectivity. The novel N-substituted alkoxyethylamines have the formula $Ar-CH(OH)-CH_2-NH-CH_2CH_2-OR_1$ (III), wherein Ar and $R_1$ have the meaning set forth herein. These novel compounds are themselves reactive, and among other things, they are useful in the production of novel diamines, as described hereafter. When the novel N-substituted ethylamines of this invention are utilized to provide imidazoles and imidothiazoles, Ar is desirably phenyl, tolyl, xylyl, or nitrophenyl, and $R_1$ is desirably an alkyl group having from one to four carbon atoms. A particularly preferred compound is one in which Ar is phenyl and $R_1$ is methyl or ethyl.

The reaction of the arylvinyl oxide and the alkoxyethylamine can be conducted with or without an inert reaction vehicle. The reaction vehicle can serve to facilitate the mixing of the reactants, moderate the course of the reaction, and improve thermal control of the reaction. Suitable reaction vehicles include hydrocarbons and halogenated hydrocarbons. The reaction vehicles are chosen with a view toward maintaining the particular temperature and pressure conditions desired in the reaction so that undue volatility is avoided, while recovery of the product is facilitated. The hydrocarbons can include aliphatic, cycloaliphatic, and aromatic hydrocarbons. The desirable hydrocarbons are saturated aliphatic hydrocarbons having from about five to about 12 carbon atoms, mononuclear and substituted mononuclear cycloaliphatics such as cyclohexane, cyclooctane, methylcyclohexane, and the like; and mononuclear aromatics and substituted mononuclear aromatic compounds such as benzene, toluene, xylene, chlorobenzene, and the like. The halogenated hydrocarbons contemplated for use in certain embodiments include lower halogenated hydrocarbons containing from one to four carbon atoms, such as methylene chloride, carbon tetrachloride, ethylene dichloride, and the like. It has also been found very useful in certain embodiments of the invention to utilize an excess of alkoxyethylamine as the reaction vehicle.

The quantity of alkoxyethylamine is desirably at least sufficient on a molar basis to react with all of the arylvinyl oxide; that is to say, the alkoxyethylamine is used in amounts which are at least stoichiometric. When the alkoxyethylamine is used as a reaction vehicle, it can be present in substantial molar excess. The use of very large molar excesses creates the need to remove extra quantities of the starting alkoxyethylamine, although it is desirable to have sufficient to provide good reaction completeness. Thus, the quantity of alkoxyethylamine is from about one to about 15 times the molar quantity of the arylvinyl oxide, and in certain preferred embodiments, it is from about five to about ten molar quantities.

The reaction can be carried out by adding the arylvinyl oxide to the excess alkoxyethylamine. The reaction can be carried out over a wide temperature range, depending upon the reaction velocity with the particular reactants and upon the pressures utilized. Generally, the temperature is controlled to provide a smooth reaction during the initial contact of the reactants, and subsequently, if desired, the temperature can be raised to ensure good reaction completeness. The temperatures utilized can be from 0° to 150° C., and preferred reaction temperatures are in the range of from 50° to 100° C. In certain preferred embodiments, the reaction is carried out under reflux of the alkoxyethylamine.

The reaction can be carried out over a range of pressures from subatmospheric to superatmospheric. Generally, no advantage accrues through the use of subatmospheric pressures, and it is accordingly desirable to use atmospheric or superatmospheric pressures up to three atmospheres. In certain particularly preferred embodiments, the reaction is carried out at reflux under atmospheric pressure.

The novel N-substituted alkoxyethylamine can be recovered or any excess alkoxyethylamine can be removed, and the product is capable of being utilized directly in a further process according to the present invention.

The novel N-substituted alkoxyethylamine produced can be reacted with a nitrile having the formula $R_2-C\equiv N$ (IV), where $R_2$ is hydrogen, aliphatic, or aromatic. The desirable aromatic groups are phenyl or substituted phenyl including lower alkyl mono- and polysubstituted phenyl, mono- and polyhalo phenyl, and the like. A preferred nitrile is benzonitrile.

The aliphatic nitrile is desirably a lower alkyl nitrile containing from two to about seven carbon atoms per molecule. The use of longer chain or unsaturated nitriles can complicate the process and increase the cost of the raw materials without any concomitant benefit. It is especially desirable to utilize the lower nitriles, such as acetonitrile and, as taught above, benzonitrile in certain preferred embodiments of the invention.

This reaction is carried out in the presence of a protic source with a reaction vehicle which is desirably aqueous. The requisite hydrogen ions are furnished through the use of a relatively strong aqueous acid. It is desirable to utilize an aqueous solution of a strong mineral acid, such as sulfuric acid, hydrochloric acid, and the like. The concentration of the mineral acid can range from about 50% by weight to the concentrated acid. Thus, a preferred protic source is concentrated sulfuric acid.

The reaction can be carried out with amounts of the nitrile ranging from equimolar, based upon the N-substituted ethylamine, up to an excess of ten times. When the nitrile is used in excess, it serves as a vehicle for the reaction, with attendant benefits in moderating and controling the course of the reaction.

The reaction can be carried out at temperatures which provide reasonable reaction rates, while at the same time permitting control of the reaction velocity. In certain embodiments of the invention, it is desirable to use a temperature of from −25° to 60° C. The acid can be added to the nitrile at a lower temperature, and after acid addition is complete, the N-substituted ethylamine is slowly added to the nitrile and acid, desirably at a slow rate with good agitation. The addition of the amine is preferably carried out at temperatures up to 10° C., and after addition is complete, the temperature can be allowed to rise to room temperature (say, 18°-22° C.) or higher, depending upon the particular reactants.

The reaction can be conducted over a wide range of pressures from subatmospheric to superatmospheric, and it has generally been found desirable to utilize atmospheric pressure. The reaction can also be effected in the presence of an inert reaction vehicle, such as those described for the preparation of the N-substituted alkoxyethylamine itself.

This process for reacting the N-substituted alkoxyethylamine and the nitrile provides novel N-(acylamino)-alkoxyethylamines having the formula $$R_2—CO—NH—CH(Ar)—CH_2—NH—CH_2CH_2—OR_1 \quad (V)$$

wherein Ar, $R_1$, and $R_2$ have the meaning set forth above. At this point amidoamine V can be obtained by neutralization, extraction with a suitable solvent, and solvent evaporation or other conventional recovery techniques. It is reactive, and is useful, among other utilities, as an intermediate. It can also be hydrolyzed without recovery as detailed herein to provide the corresponding diamine.

The novel diamine, having the formula $$NH_2—CH(Ar)—CH_2—NH—CH_2CH_2—OR_1 \quad (VI)$$

wherein Ar and $R_1$ have the meaning set forth herein, can be obtained from Compound V by hydrolysis with a base or a protic source. The desirable protic sources are strong acids, such as mineral acids, or bases such as alkali metal hydroxides. Sulfuric acid is a preferred mineral acid, and sodium and potassium hydroxides are preferred bases. These protic sources or bases are desirably used in an aqueous milieu. Thus, a 10 to 50% aqueous sulfuric acid and a 5 to 50% alkali metal hydroxide have been found to provide good results in practicing this process.

The hydrolysis can be carried out over a range of temperatures from 0° to about 110° C. Generally, an initial reaction at a higher temperature, followed by a lower temperature over a longer period of time provides desirable reaction completeness. Accordingly, refluxing with the aqueous protic source or base for from one to six hours, followed by further contact at 20°—30° C. for from 8—24 hours, provides good reaction completeness.

This reaction can be carried out over a range of pressures from subatmospheric to superatmospheric. Generally, no advantage is obtained in this process for hydrolysis by operating at subatmospheric pressures, while in some cases the reaction can be accelerated by operation at superatmospheric pressures. It is generally found, however, that atmospheric pressure provides adequate velocity and completeness, and such pressure is preferred.

The novel diamine VI and the processes for producing it, together with its novel predecessor intermediates, are the key to a regioselective synthesis of imidazothiazoles, one of the more prominent of which is tetramisole. Such a diamine can be converted to tetramisole and related compounds. A particularly preferred embodiment involves the reaction of diamine VI with carbon disulfide to produce a dithiocarbamate intermediate which can be represented by the tautomer $$^\ominus SC(S)—NH—C(Ar)—CH_2—^\oplus NH_2—CH_2CH_2—OR_1 \quad (VII)$$

followed by cyclization with heat to produce 1-substituted-4-arylimidazolidin-2-thione having the formula

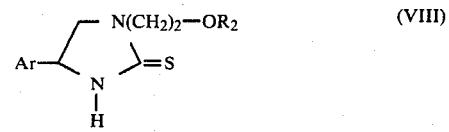

The thione so produced is then treated with an acid having a pharmaceutically acceptable anion to provide imidazothiazole:

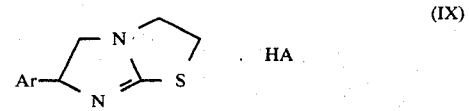

It will be recognized that these are the pharmaceutically acceptable salts of d,l-6-aryl-2,3,5,6-tetrahydroimidazo-[2,1-b]thiazole. When Ar is phenyl, the product is tetramisole. Such acid compounds can be neutralized with a base to provide the free thiazole (X), when this is desired.

The dithiocarbamate is prepared by reacting diamine (VI) with carbon disulfide at temperatures of from −10° to 40° C. It is generally desirable to use from a 50 to 100% stoichiometric excess of carbon disulfide. This reaction step is desirably carried out in the presence of an inert vehicle such as one or more hydrocarbons or chlorinated hydrocarbons. Preferred hydrocarbons include lower alkyl, cycloalkyl, and aromatic materials such as benzene, toluene, xylene, and the like; liquid aliphatic hydrocarbons having five to 12 carbon atoms such as hexane, isooctane, heptane and the like; and cycloaliphatic materials such as cyclohexane, cyclooctane, and the like. The chlorinated hydrocarbons include the polyhalogenated lower aliphatic materials, a preferred vehicle being tetrachloroethane.

The reaction time ranges from about 30 minutes to about four hours in certain desirable embodiments of the invention. The resulting dithio compound VII is cyclized by heating at 80° to 150° C. The ring closure to provide thione VIII is carried out for from about two to about 20 hours. Production of pharmaceutically acceptable salt of the tetramisole is then effected on the thione by acid treatment to close the thiazolidine ring.

It will be understood from the present disclosure that the various intermediates can be recovered and purified as desired by conventional techniques such as extraction, solvent evaporation, water washing, and combinations of these conventional procedures. Further, the various steps can be carried out under subatmospheric or superatmospheric pressure. Unless superatmospheric pressure is desirable because of the volatility of a solvent or reactant, it is generally preferred to conduct all of the steps under atmospheric pressure. This provides further economy in not requiring special pressure vessels and handling techniques in commercial production.

As taught herein, intermediates and imidazothiazoles can be prepared with a variety of aromatic substituents. In a particularly preferred embodiment for the preparation of tetramisole, the aryl group is phenyl.

The following Examples are given to illustrate embodiments of the invention as it is presently preferred to practice it. It will be understood that these Examples are illustrative, and the invention is not to be considered as restricted thereto except as indicated in the appended Claims.

EXAMPLE I

Preparation of N-(2-Hydroxy-2-phenylethyl)-2-methoxyethylamine

To 157 g of refluxing 2-methoxyethylamine is added dropwise 25 g styrene oxide during a period of 15 minutes. After addition of the amine, the mixture is allowed to reflux for another two hours.

The reflux condenser is then replaced by a distillation head and the excess 2-methoxyethylamine is distilled off at atmospheric pressure. The last traces of 2-methoxyethylamine are distilled off under reduced pressure, and the residual solid is triturated with 100 ml of hexane.

The resulting material is filtered to provide the above-designated N-methoxyethyl derivative with a melting point of 6°–70° C. IR (infrared) and NMR (proton nuclear magnetic resonance) spectroscopy confirm the structure.

EXAMPLE II

Preparation of N-(2-Hydroxy-2-phenylethyl)-2-methoxyethylamine

Methoxyethylamine in the amount of 157 g (2.09 moles) is brought to reflux with a bath temperature of 110°–120° C., and 25 g (0.208 moles) of styrene oxide is added during a period of 15 minutes. The mixture is thereafter refluxed gently for two hours.

The reflux condenser is then replaced by a distillation head and excess amine is distilled off at atmospheric pressure. During this time the bath temperature is slowly raised to about 150° C. The last traces of amine are distilled off under vacuum.

The residue is analyzed by VPC (vapor-phase chromatography) and NMR, and is found to contain more than 95% of N-(2-methoxyethyl)-2-phenyl-2-hydroxyethylamine. Upon cooling, the residue crystallizes to provide a solid which is triturated with hexane and filtered to obtain 37 g of the aforesaid product with a melting point of 68°–70° C. This is a 91.2% yield, based on the styrene oxide. About 98% (138 g) of the amine is recovered.

EXAMPLE III

Preparation of N-(2-Acetylamino-2-phenethyl)-2-methoxyethylamine

A flask is charged with 12.3 g (0.3 moles) of acetonitrile which is cooled to 0° C. and maintained at a temperature of from 0° to 5° C., utilizing a bath temperature of −10° to −20° C. Thereafter, 80 g (0.82 moles) of concentrated sulfuric acid is added dropwise, and 19.5 g (0.1 mole) of the N-substituted hydroxyethylamine produced in Example II is added in small portions with efficient magnetic stirring so as to maintain the temperature between 0° and 10° C. The addition consumes about 30 to 35 minutes.

The reaction mixture is then stirred at 0° C. for one hour and at 25° C. for one and a half hours. Thereafter, the reaction mixture is poured over 50 g of ice, and the resulting solution is added dropwise to 100 g of sodium hydroxide in 300 ml of water, while cooling in an ice bath with efficient magnetic stirring. The solution is extracted twice with 125 ml portions of methylene chloride. The two extracts are washed with water and dried over sodium sulfate.

The solvent is evaporated to provide 19.6 g of the amidoamine stated above. IR analysis shows a satisfactory result for an amidoamine and the NMR is totally consistent with this compound.

EXAMPLE IV

Preparation of N-(2-Amino-2phenyl)-2-methoxyethylamine

A flask is charged with a total of 23.6 g (0.1 mole) of the amidoamine produced in Example III and refluxed with 150 g of 20% aqueous sulfuric acid for three hours. Following the reflux, the reaction mixture is stirred at room temperature of about 22° C. for an overnight period of 16 hours. The mixture is then neutralized to about pH 10 with cooling, utilizing sufficient 40% aqueous sodium hydroxide.

The reaction mixture is thrice extracted with 75 ml portions of methylene chloride. The extracts are then washed with water and dried over sodium sulfate. The solvent is stripped off to provide about 18.0 g of yellow oil. The IR is consistent with the desired diamine. The yellow oil is then distilled under reduced pressure.

The distillation produces 16.8 g of a liquid with a boiling point of 130°–135° C. at 1 mm Hg.

EXAMPLE V

A flask is charged with 37.2 g (0.90 mole) of acetonitrile and cooled to 0° C., whereupon 100 ml (180 g, or 1.84 moles) of concentrated sulfuric acid is added dropwise, while the temperature is maintained between 0° and 10° C. utilizing a −10° to 0° C. bath. After completion of the acid addition, 58.5 g (0.3 mole) of 2-phenyl-2-hydroxy-N-(2-methoxyethyl)ethylamine is added in portions over 35 minutes, while the temperature is still maintained between 0° and 10° C. with the aforesaid cooling bath. Following addition of the amine, the mixture is stirred at 0° to 25° C. for 90 minutes and then added to 300 ml of water. The aqueous material is refluxed for four hours, cooled, and stirred overnight at room temperature.

The cooled material is then neutralized to a pH of about 10 utilizing sufficient 40% aqueous sodium hydroxide and cooling. The neutralized product is extracted thrice with 200 ml quantities of methylene chloride. The methylene chloride extracts are washed and dried over sodium sulfate and concentrated to provide 53.6 g of oil. The IR spectrum indicates that a diamine is obtained.

The oil is distilled under vacuum to provide 48.2 g colorless liquid 2-amino-2-phenyl-N-(2-methoxyethyl)ethylamine having a boiling point of 110°—115° C. at 0.1-0.2 mm Hg. This represents an 82.8% yield, based upon the hydroxyethylamine starting material.

EXAMPLE VI

Preparation of 2-Amino-2-phenyl-N-(2-methoxyethyl)ethylamine

A flask is charged with 43 g of benzonitrile and cooled to 0° C., whereupon 100 g of concentrated aqueous sulfuric acid is added dropwise, while the temperature is maintained between 0° and 10° C. utilizing a −10° to 0° C. cooling bath. After completion of the acid addition, 25 g of 2-phenyl-2-hydroxy-N-(2-methoxyethyl)ethylamine is added in portions over 45 minutes while the temperature is still maintained between 0° and 10° C. with the aforesaid cooling bath. Following addition of the amine, the mixture is stirred at 0° to 25° C. for 90 minutes and then added to 400 ml of water. The unreacted benzonitrile is extracted twice with 200 ml portions of methylene chloride and the aqueous material is refluxed for 24 hours.

The cooled material is thereupon neutralized to a pH of about 10 with 40% aqueous sodium hydroxide, while cooling. The neutralized product is extracted thrice with 100 ml quantities of methylene chloride. The methylene chloride extracts are washed, dried over sodium sulfate, and concentrated to provide 19 g of oil. The oil is distilled under vacuum to provide 13 g of colorless liquid 2-amino-2-phenyl-N-(2-methoxyethyl)ethylamine having a boiling point of 110°–115° C. at 0.1–0.2 mm Hg.

EXAMPLE VII

Preparation of 1-(2-Methoxyethyl)-4-phenylimidazolidin-2-thione

A flask is charged with 6.85 g of N-(2-amino-2-phenethyl)-2-methoxyethylamine in 20 ml of xylene, and this material is stirred with 3 ml of carbon disulfide at room temperature for two hours. The resulting slurry is then heated to 130° C. and maintained at this temperature for four hours. The xylene is then distilled off under reduced pressure, and the thione product is identified by IR and NMR spectroscopic methods.

EXAMPLE VIII

Preparation of D,L-Tetramisole

A flask is charged with 4.3 g of 1-(2-hydroxyethyl)-4-phenylimidazolidin-2-thione suspended in 50 ml of concentrated hydrochloric acid. The mixture is slowly heated to 70° C. with magnetic stirring and maintained at this temperature for 10 hours. Thereafter, the flask contents are cooled and stirred at room temperature overnight.

The resulting solution is diluted with 50 ml of water, and the impurities are extracted with two 30 ml portions of methylene chloride. The aqueous layer is rendered basic with ammonium hydroxide and then extracted with three 50 ml portions of methylene chloride. The methylene chloride extracts are washed and dried. The solvent is evaporated to provide an oil which crystallizes. This oil is identified as (±) 6-phenyl-2,3,5,6-tetrahydroimidazo [2, 1-b]thiazole by IR and NMR spectroscopy.

What is claimed is:

1. A process for the preparation of tetramisole which comprises the steps of:

(a) reacting at least equimolar quantities of an arylvinyl oxide having the formula:

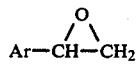

with an alkoxyethylamine having the formula: $R_1$—O—($CH_2$ at a temperature of from 0°–150° C. to obtain an N-(arylhydroxyalkyl)alkoxyethylamine having the formula: Ar—CH(OH)—CH$_2$—NH—CH$_2$CH$_2$—OR$_1$, wherein Ar is phenyl and R$_1$ is a lower alkyl group, (b) reacting the latter N-substituted alkoxyethylamine in the presence of a mineral acid with a nitrile having the formula R$_2$C|N, where R$_2$ is hydrogen, alkyl, or aryl at a temperature of from −25° to 60° C. to obtain an amidoamine having the formula: R$_2$—C0—NH—CH(Ar)—CH$_2$—NH—CH$_2$CH$_2$—OR$_1$, where Ar, R$_1$, and R$_2$ are the same as hereinabove defined, (c) hydrolyzing the latter amidoamine with an aqueous inorganic base or a mineral acid at a temperature ranging from about 0° C. to about 110° C. for a period of from one to six hours to obtain a diamine having the formula: NH$_2$—CH(Ar)—CH$_2$—NH—CH$_2$CH$_2$—OR$_1$ where R$_1$ and Ar are as above defined, (d) reacting the resultant diamine with carbon disulfide in an inert organic solvent at a temperature ranging from about −10° C. to about 40° C. to obtain a dithiocarbamate, (e) heating the latter dithiocarbamate at a temperature ranging from about 80° C. to about 150° C. for from two to twenty hours in an inert organic solvent to produce a thione having the formula:

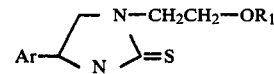

(f) further reacting the latter resultant thione with an acid having the formula HA to provide an imidazothiazole having the formula:

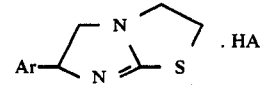

where Ar is phenyl and A is an anion of a pharmaceutically acceptable acid, and (g) thereafter, neutralizing said tetramisole salt with an aqueous inorganic base to obtain tetramisole per se.

2. The process according to claim 1 wherein the reaction is carried out at from 0° to 150° C.

3. The process according to claim 1 wherein the reaction is carried out in an inert organic solvent.

4. The process according to claim 3 wherein the organic solvent is selected from the group consisting of a saturated aliphatic hydrocarbon having up to 12 carbon atoms, a cycloaliphatic hydrocarbon and alkyl-substituted cyclo- aliphatic hydrocarbon, mononuclear aryl and alkyl- and nitro- substituted mono- and polynuclear aryl hydrocarbon, and mixtures thereof.

5. The process according to claim 1 wherein the alkoxyethylamine ranges from stoichiometric up to 15 times the molar quantity of the arylvinyl oxide.

UNITED STATES PATENT OFFICE
CERTIFICATE OF CORRECTION

Patent No. 4,245,103      Dated January 13, 1981

Inventor(s) SIVARAMAN RAGHU

It is certified that error appears in the above-identified patent and that said Letters Patent are hereby corrected as shown below:

Column 9, line 58, delete "$O-(CH_2$" and substitute -- $O-(CH_2)_2-NH_2$ --.

Column 10, line 5, delete "$R_2C|N$" and substitute -- $R_2C \equiv N$ --.

Signed and Sealed this

Fourteenth Day of April 1981

[SEAL]

*Attest:*

RENE D. TEGTMEYER

*Attesting Officer*     *Acting Commissioner of Patents and Trademarks*